United States Patent [19]

Schefczik

[11] 3,950,340

[45] Apr. 13, 1976

[54] QUINAZOLINE DYES

[75] Inventor: Ernst Schefczik, Ludwigshafen, Germany

[73] Assignee: Badische Anilin- & Soda-Fabrik Aktiengesellschaft, Ludwigshafen (Rhine), Germany

[22] Filed: July 24, 1973

[21] Appl. No.: 382,275

[30] Foreign Application Priority Data

July 29, 1972  Germany............................ 2237372

[52] U.S. Cl....... 260/256.4 Q; 260/37 N; 260/40 R; 260/247.1 L; 260/251 Q; 260/268 C; 260/293.62; 260/319.1; 260/326.4
[51] Int. Cl.².................................... C07D 487/06
[58] Field of Search..... 260/256.4 Q, 251 Q, 251 A, 260/247.1 L

[56] References Cited
UNITED STATES PATENTS 3,684,808   8/1972   Ulrich.......................... 260/256.4 Q

*Primary Examiner*—R. Gallagher
*Assistant Examiner*—David E. Wheeler
*Attorney, Agent, or Firm*—Johnston, Keil, Thompson & Shurtleff

[57] ABSTRACT

Dyes of the formula:

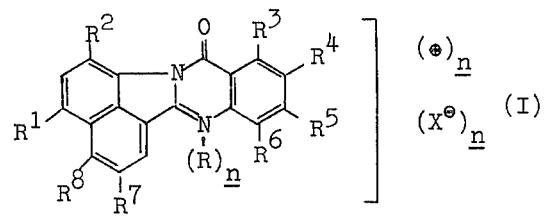

in which
R is unsubstituted or substituted alkyl or aralkyl;
$R^1$ to $R^6$ is each hydrogen or a substituent;
$R^7$ is hydrogen or alkoxy;
$R^8$ is hydrogen or alkoxy;
$n$ is zero or 1;
$X^-$ is an anion; and
$R^1$ and $R^8$ may together be a radical:

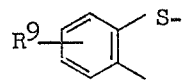

where $R^9$ is hydrogen, alkyl or alkoxy; and at least one of the radicals $R^1$ to $R^6$ is arylmercapto.
The dyes give bright colorations, particularly on polyesters and in resins.

3 Claims, No Drawings

QUINAZOLINE DYES

The invention relates to dyes of the formula (I):

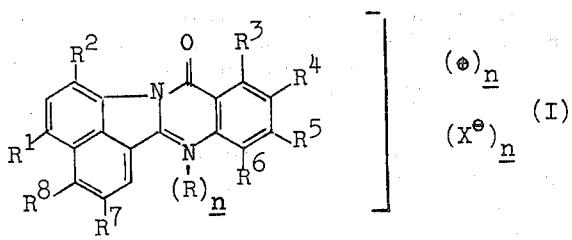

in which
R is unsubstituted or substituted alkyl or aralkyl;
each of $R^1$ to $R^6$ is hydrogen or a substituent;
$R^7$ and $R^8$ is each hydrogen or alkoxy;
n is zero or 1;
$X^-$ is an anion;
$R^1$ and $R^8$ together may be a radical:

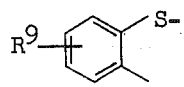

where $R^9$ is hydrogen, alkyl or alkoxy; and
at least one of the radicals $R^1$ to $R^6$ is arylmercapto.

Examples of radicals R are ethyl, benzyl, β-hydroxy-γ-chloropropyl and particularly methyl, β-hydroxyethyl and β-hydroxypropyl.

Examples of substituents $R^1$ to $R^6$ are alkyl, halogen, alkoxy, phenoxy, C-acyl, unsubstituted or substituted carbamoyl or sulfonamido, carboxyl, carbalkoxy and arylmercapto.

Specific examples are as follows:
for $R^1$:
chloro, methyl, methoxy, ethoxy, phenoxy, benzoyl, benzoyl bearing chloro, bromo, methyl, methoxy or cyano as a substituent, sulfonamido, sulfonamido bearing methyl, ethyl, propyl, butyl, β-hydroxyethyl, γ-methoxypropyl or β-ethylhexyl as one or two substituents on the nitrogen atom, sulfopyrrolidide, sulfopiperidide, sulfomorpholide, sulfopiperazide, naphthylmercapto and particularly phenylmercapto, o-aminophenylmercapto and also their derivatives bearing chloro, methyl, methoxy, ethoxy, acetylamino, trifluoromethyl or carbalkoxy (methoxy, ethoxy, butoxy, β-hydroxyethoxy or β-methoxyethoxy) as substituents;
for $R^2$:
chloro or the arylmercapto radicals specified for $R^1$;
for $R^3$:
chloro, methyl, carboxyl, carbamoyl, carbamoyl bearing on the nitrogen atom one or two of the substituents methyl, ethyl, propyl, butyl, β-hydroxyethyl, γ-methoxypropyl and β-ethoxyhexyl, carbopyrrolidide, carbopiperidide, carbomorpholide, carbopiperazide, carbomethoxy, carboethoxy, carbopropoxy, carbobutoxy, carbo-β-ethylhexoxy, carbo-β-hydroxyethoxy, carbo-ω-hydroxyhexoxy, carbo-β-methoxyethoxy, carbo-β-butoxyethoxy or carbo-β-(β'-methoxyethoxy)ethoxy, benzoyl, benzoyl bearing chloro, bromo, methyl or methoxy as a substituent and also the arylmercapto radicals enumerated for $R^1$;
for $R^4$:
chloro, bromo, nitro, methyl, methoxy and ethoxy and the ester, carbamoyl and arylmercapto radicals specified for $R^3$;
for $R^5$:

methoxy and ethoxy and the carboxylic acid derivatives specified for $R^3$ and the arylmercapto radicals specified for $R^1$;
for $R^6$:
chloro, bromo, nitro, methyl and methoxy and arylmercapto radicals specified for $R^1$.

Examples of alkoxy radicals $R^7$, $R^8$ and $R^9$ are: methoxy and ethoxy; alkyl radicals $R^9$ are preferably methyl.

The dyes of the formula (I) preferably have one or two arylmercapto groups, the radical possibly formed from $R^1$ and $R^8$ together being included.

Examples of anions are: chloride, bromide, sulfate, methosulfate, ethosulfate, formate, acetate and tetrachlorozincate.

The new dyes are greenish yellow to red violet and give bright deep colorations having good to very good fastness properties, particularly fastness to light and heat setting, on polyesters (n = 0) and acrylonitrile polymers (n = 1). Some of the dyes are also suitable for the mass coloration of plastics, for example of polystyrene, polycarbonates and polyesters.

Dyes of the formula (I) may be produced by reacting a compound of the formula (II):

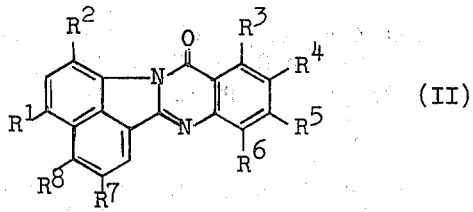

in which the radicals $R^1$ to $R^8$ have the above meanings other than arylmercapto and at least one of the radicals $R^1$ to $R^6$ is chloro or preferably bromo with an arylmercaptan with replacement of the halogen and if desired quaternizing the reaction product.

Compounds of the formula (II) are accessible by methods analogous to those disclosed in the literature reference Collect. Czech. Chem. Commun. volume 35, 1970, page 737 et seq.

Replacement of halogen by the arylmercapto radical in conveniently effected by reacting the components in an inert solvent in the presence of a base at an elevated temperature, for example from 100° to 250°C and preferably from 130° to 220°C. Equivalent amounts of the components or advantageously a slight excess of the arylmercaptan are used.

Examples of inert solvents are: dimethylformamide, N-methylpyrrolidone, trichlorobenzene, naphthalene, chloronaphthalene and quinoline.

Examples of bases are alkali metal hydroxides and acetates and particularly alkali metal carbonates and bicarbonates.

Compounds of the formula (I) may also be produced by condensing a compound of the formula (III):

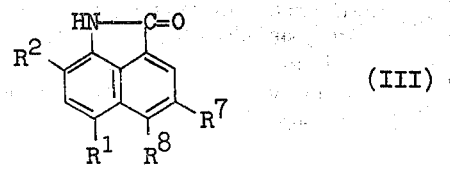

with a compound of the formula (IV):

(IV)

in which
Y is hydroxy, amino or low molecular weight alkoxy and $R^1$ to $R^8$ have the meanings given for formula (I) in the presence of water-eliminating agents and if desired quaternizing the condensation product.

Compounds of the formula (III) and their production are described in German Patent No. 2,233,937 (O.Z. 29,284), these compounds thus being obtained for example by reacting a compound of the formula in which $X^1$ is hydrogen, chloro or bromo and at least one $X^1$ is halogen, $R^7$ and $R^8$ being hydrogen, methoxy or ethoxy, with a compound of the formula Ar — SH or a salt thereof, particularly an alkali metal salt of an arylthiol, Ar being an unsubstituted or substituted phenyl or naphthyl. Compounds are also obtained where $R^8$ is combined with the adjacent $X^1$ to form the group with $R^9$ being hydrogen, alkyl or alkoxy.

Water-eliminating agents include for example: phosphorus trichloride or phosphorus pentachloride and particularly phosphorus oxychloride.

The condensation reaction may conveniently be carried out by reacting equivalent amounts of the components in a solvent which is inert under the reaction conditions at a temperature of from about 50° to 150°C, preferably from 80° to 130°C.

Examples of suitable solvents are: benzene, toluene, chlorobenzene, nitrobenzene, trichloroethylene, perchloroethylene and also phosphorus oxychloride.

Compounds of the formula (I) in which $n$ is equal to 1 are prepared by quaternizing a compound with $n$ equal to zero by a conventional method.

Examples of quaternizing agents are alkyl halides, aralkyl halides, arylsulfonic esters and particularly dialkyl sulfates and epoxides. Specific examples are: methyl iodide, butyl bromide, benzyl chloride, methyl toluenesulfonate, ethyl toluenesulfonate, dimethyl sulfate, diethyl sulfate, ethylene oxide, propylene oxide and epichlorohydrin.

Compounds of the formula (I) in which $R^1$ and $R^8$ together form a radical:

may be prepared from the corresponding o-aminoarylmercapto compounds, for example by the method of German Patent 1,297,259. The same is true of the cyclized compounds of the formula (III).

Dyes of the formula (I) are preferred which have an optionally cyclized arylmercapto group in the naphtholactam radical and a substituent of the second order in the anthranilic acid radical. Examples of substituents of the second order are nitro, carboxyl, carbalkoxy, carbamoyl, N-monosubstituted carbamoyl, N,N-di-substituted carbamoyl and aroyl.

$R^7$ and $R^8$ and two or three of the radicals $R^3$ to $R^6$ are preferably hydrogen; $n$ is preferably zero; and $R^1$ is preferably arylmercapto.

Particularly valuable dyes have $R^1$ equal to aroyl and $R^1$ and/or $R^6$ arylmercapto, the remaining substituents being hydrogen.

Details of the production will be found in the Examples in which parts and percentages are by weight unless stated otherwise.

EXAMPLE 1

A mixture of 1500 parts by volume of dimethylformamide, 349 parts of a compound of the formula (V)

120 parts of thiophenol and 150 parts of anhydrous potassium carbonate is boiled under reflux for eight hours. During cooling 1000 parts of 5% acetic acid is allowed to flow in, the reaction product crystallizing out. It is suction filtered, washed with water and dried at 100°C. 368 parts of a dye of the constitution (VI) is obtained:

(VI)

which colors polyester greenish yellow hues having good fastness properties. The same dye is obtained by using the corresponding chloro compound instead of bromobenzoindoloquinazolone (V). Since the chloro compound reacts more slowly it is convenient to double the reaction period or to carry out the reaction in a solvent having a higher boiling point, as for example N-methylpyrrolidone.

The starting material of the constitution (V) is prepared as follows.

A mixture of 248 parts of 5-bromo-1,8-naphtholactam and 137 parts of anthranilic acid is introduced in portions into 1000 parts of phosphorus oxychloride at 80° to 90°C. The whole is boiled under reflux while stirring and then decomposed by stirring into ice. The precipitated product is suction filtered, washed with hot water and dried. 339 parts of (V) having a bromine content of 22.5% (calculated 22.9%) and a melting point of 325°C (recrystallized from nitrobenzene) is obtained.

Dyes of the formula (VII) identified by their substituents in the following Table may be obtained analogously to Example 1:

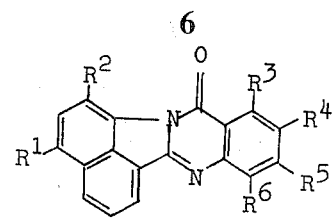

(VII)

Table 1

| Ex. | $R^1$ | $R^2$ | $R^3$ | $R^4$ | $R^5$ | $R^6$ | Shade on polyester |
|---|---|---|---|---|---|---|---|
| 2 | $-SC_6H_4CH_3$ (4') | H | H | H | H | H | yellow |
| 3 | $-SC_6H_4OCH_3$ (4') | H | H | H | H | H | yellow |
| 4 | $-SC_6H_4Cl$ (4') | H | H | H | H | H | greenish yellow |
| 5 | $-SC_6H_3Cl_2$ (2',5') | H | H | H | H | H | greenish yellow |
| 6 | $-SC_6H_4COOCH_3$ (4') | H | H | H | H | H | yellow |
| 7 | $-SC_6H_5$ | $-SC_6H_5$ | H | H | H | H | yellow |
| 8 | $-SC_6H_4OCH_3$ (4') | $-SC_6H_4OCH_3$ (4') | H | H | H | H | yellow |
| 9 | H | H | H | $-SC_6H_5$ | H | H | greenish yellow |
| 10 | H | H | H | $-SC_6H_5CH_3$ (4') | H | H | greenish yellow |
| 11 | H | H | H | H | $-SC_6H_5$ | H | greenish yellow |
| 12 | H | H | H | H | H | $-SC_6H_5OCH_3$ (4') | greenish yellow |
| 13 | $-SC_6H_5$ | H | H | $-SC_6H_5$ | H | H | yellow |
| 14 | $-SC_6H_4CH_3$ (4') | H | H | $-SC_6H_4CH_3$ (4') | H | H | yellow |
| 15 | $-SC_6H_5$ | H | H | H | $-SC_6H_5$ | H | yellow |
| 16 | $-SC_6H_4Cl$ (4') | H | H | H | H | $-SC_6H_4Cl$ (4') | yellow |
| 17 | H | H | $-SC_6H_5$ | H | H | $-SC_6H_5$ | greenish yellow |
| 18 | H | H | $-SC_6H_5$ | $-SC_6H_5$ | H | H | greenish yellow |
| 19 | H | H | H | $-SC_6H_5$ | $-SC_6H_5$ | H | greenish yellow |
| 20 | H | H | H | $-SC_6H_5$ | H | $-SC_6H_5$ | greenish yellow |
| 21 | H | H | H | $-SC_6H_4CH_3$ (4') | H | $-SC_6H_4CH_3$ (4') | greenish yellow |
| 22 | H | H | H | $-SC_6H_4OCH_3$ (4') | H | $-SC_6H_4OCH_3$ (4') | greenish yellow |
| 23 | H | H | H | $-SC_6H_4CF_3$ (3') | H | $-SC_6H_4CF_3$ (3') | greenish yellow |
| 24 | $-CH_3$ | H | H | $-SC_6H_5$ | H | H | yellow |
| 25 | $-OCH_3$ | H | H | $-SC_6H_4CH_3$ (4') | H | H | yellow |
| 26 | $-OC_2H_5$ | H | H | $-SC_6H_4Cl$ (4') | H | H | yellow |
| 27 | $-COC_6H_5$ | H | H | $-SC_6H_5$ | H | H | greenish yellow |
| 28 | $-COC_6H_5$ | H | H | $-SC_6H_4Cl$ (4') | H | H | greenish yellow |
| 29 | $-COC_6H_4Cl$ (4') | H | H | $-SC_6H_4CH_3$ (4') | H | H | greenish yellow |
| 30 | $-COC_6H_3Cl_2$ (2',5') | H | H | $-SC_6H_5$ | H | H | greenish yellow |
| 31 | $-COC_6H_4CH_3$ (4') | H | H | H | H | $-SC_6H_5$ | greenish yellow |
| 32 | $-SO_2N(CH_3)_2$ | H | H | $-SC_6H_4Cl$ (4') | H | H | yellow |
| 33 | $-SO_2N\text{(pyrrolidine)}$ | H | H | $-SC_6H_5CH_3$ (4') | H | H | yellow |
| 34 | $-SO_2N\text{(piperidine)}$ | H | H | $-SC_6H_4OCH_3$ (4') | H | H | yellow |
| 35 | $-SO_2N\text{(morpholine)}$ | H | H | $-SC_6H_5$ | H | H | yellow |
| 36 | $-COC_6H_5$ | H | H | $-SC_6H_5$ | H | $-SC_6H_5$ | greenish yellow |
| 37 | $-COC_6H_5$ | H | H | $-SC_6H_4OCH_3$ (4') | H | $-SC_6H_4OCH_3$ (4') | reddish yellow |
| 38 | $-SO_2N(C_2H_5)_2$ | H | H | $-SC_6H_5$ | H | $-SC_6H_5$ | yellow |
| 39 | $-SO_2N(C_4H_9)_2$ | H | H | $-SC_6H_4Cl$ (4') | H | $-SC_6H_4Cl$ | greenish |

Table 1-continued

| Ex. | R¹ | R² | R³ | R⁴ | R⁵ | R⁶ | Shade on polyester |
|---|---|---|---|---|---|---|---|
| 40 | SO₂N◯ | H | H | —SC₆H₅ (4') | H | —SC₆H₅ | yellow |
| 41 | —SC₆H₄CH₃ (4') | H | CH₃ | H | H | H | yellow |
| 42 | —SC₆H₅ | —SC₆H₅ | CH₃ | H | H | H | yellow |
| 43 | —SC₆H₄OCH₃ (4') | H | H | CH₃ | H | H | yellow |
| 44 | —SC₆H₄CH₃ (4') | —SC₆H₄CH₃ (4') | H | CH₃ | H | H | yellow |
| 45 | —SC₆H₄OCH₃ (4') | —SC₆H₄OCH₃ (4') | H | CH₃ | H | H | reddish yellow |
| 46 | —SC₆H₅ | H | H | H | H | CH₃ | yellow |
| 47 | —SC₆H₅ | H | H | OCH₃ | H | H | reddish yellow |
| 48 | —SC₆H₅ | H | H | OC₂H₅ | H | H | reddish yellow |
| 49 | —SC₆H₅ | —SC₆H₅ | H | OC₂H₅ | H | H | reddish yellow |
| 50 | —SC₆H₄Cl (4') | H | H | H | OCH₃ | H | yellow |
| 51 | —SC₆H₅ | H | H | H | OC₂H₅ | H | yellow |
| 52 | —SC₆H₅ | H | H | H | H | OCH₃ | yellow |
| 53 | —SC₆H₄Cl (4') | H | H | H | H | OCH₃ | yellow |
| 54 | —SC₆H₅ | —SC₆H₅ | H | H | H | OCH₃ | yellow |
| 55 | —SC₆H₅ | H | —COOC₂H₅ | H | H | H | greenish yellow |
| 56 | —SC₆H₅ | H | —COO(CH₂)₂OH | H | H | H | greenish yellow |
| 57 | —SC₆H₄CH₃ (4') | H | —CONH(CH₂)₃OCH₃ | H | H | H | yellow |
| 58 | —SC₆H₅ | H | —CON◯ | H | H | H | yellow |
| 59 | —SC₆H₅ | H | —CON(C₃H₇)₂ | H | H | H | yellow |
| 60 | —SC₆H₅ | —SC₆H₅ | —COC₆H₅ | H | H | H | yellow |
| 61 | —SC₆H₅ | H | H | —COOC₄H₉ | H | H | yellow |
| 62 | —SC₆H₅ | —SC₆H₅ | H | H | —COOC₅H₁₁ | H | greenish yellow |
| 63 | —SC₆H₄Cl (4') | H | H | H | —COOCH₂CH(CH₂)₃CH₃ / C₂H₅ | H | greenish yellow |
| 64 | —SC₆H₅ | H | H | H | —CON(CH₃)₂ | H | yellow |
| 65 | —SC₆H₄CH₃ (4') | H | H | H | —CON(C₄H₉)₂ | H | reddish yellow |
| 66 | —SC₆H₅ | H | H | H | —CON◯O | H | yellow |
| 67 | —SC₆H₅ | H | H | H | —COC₆H₅ | H | yellow |
| 68 | —SC₆H₅ | H | H | H | —COC₆H₄CH₃ (4') | H | yellow |
| 69 | —SC₆H₄OCH₃ (4') | H | H | H | —COC₆H₄Cl (4') | H | reddish yellow |
| 70 | —SC₆H₅ | —SC₆H₅ | H | H | —COC₆H₃(CH₃)₂ (2',5') | H | yellow |
| 71 | —SC₆H₅ | H | H | H | —COC₆H₄OC₂H₅ (4') | H | yellow |
| 72 | —SC₆H₅ | H | H | H | H | —CON◯ | yellow |

The dyes listed in Table 2 and having the formula (VIII) are also obtained by the method of Example 1. They all give a yellow hue on polyester:

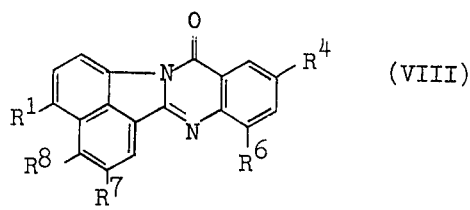

(VIII)

TABLE 2

| Example | R¹ | R⁴ | R⁶ | R⁷ | R⁸ |
|---|---|---|---|---|---|
| 73 | H | —SC₆H₅ | H | —OCH₃ | H |
| 74 | —SC₆H₅ | H | H | H | —OCH₃ |
| 75 | —SC₆H₅ | H | H | H | —OC₂H₅ |
| 76 | H | —SC₆H₅ | —SC₆H₅ | H | —OC₂H₅ |

EXAMPLE 77

349 parts of a compound of the formula (V), 140 parts of 2-aminothiophenol and 180 parts of anhydrous potassium carbonate are added in sequence to 2000 parts of molten naphthalene. The mixture is stirred for six hours at 200°C and then about 1500 parts of naphthalene is distilled off in vacuo. The residue is ground with benzene, suction filtered and washed with ethanol. The filter cake is then dispersed in 2000 parts of 2% hydrochloric acid and again suction filtered, washed with water and dried. 361 parts of a compound of the formula (IX):

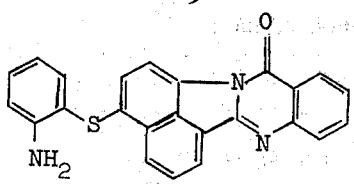

is obtained having a melting point of 290°C after having been recrystallized from dimethylformamide.

The compound of the formula (IXa):

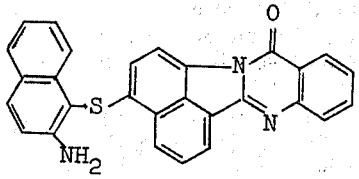

(IXa)

is also obtained analogously to Example 77.
Compounds having the constitution (X):

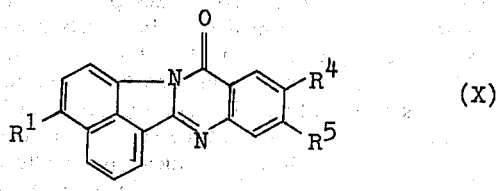

set out in Table 3 may also be prepared by the process of Example 77.

TABLE 3

| Example | $R^1$ | $R^4$ | $R^5$ |
|---|---|---|---|
| 78 | H₃C—⌬(S—)(NH₂) | H | H |
| 79 | CH₃-⌬(S—)(NH₂) | H | H |
| 80 | CH₃O—⌬(S—)(NH₂) | H | H |
| 81 | C₂H₅—⌬(S—)(NH₂) | H | H |
| 82 | ⌬(S—)(NH₂) | CH₃ | H |
| 83 | ⌬(S—)(NH₂) | H | $-COOC_5H_{11}$ |
| 84 | ⌬(S—)(NH₂) | H | $-COO(CH_2)_5OH$ |
| 85 | ⌬(S—)(NH₂) | H | $-CON(C_4H_9)_2$ |
| 86 | ⌬(S—)(NH₂) | H | $-CON\!\!\diagup\!\!\diagdown$ |
| 87 | ⌬(S—)(NH₂) | H | $-COC_6H_5$ |
| 88 | ⌬(S—)(NH₂) | H | $-CO\!-\!C_6H_4\!-\!C_4H_9$ |

EXAMPLE 89

277 parts of 5-phenylmercapto-1,8-naphtholactam and 137 parts of anthranilic acid are introduced into 1500 parts by volume of anhydrous chlorobenzene and the mixture is stirred at 100°C. 200 parts of phosphorus oxytrichloride is dripped in within thirty minutes and the whole is stirred for another four hours at 100° to 110°C. 500 parts of ethanol is then dripped in, and the whole is allowed to cool, suction filtered, washed with ethanol and dried. 289 parts of a dye of the constitution (VI) is obtained which is identical chemically and tinctorially with the dye obtained in Example 1.

EXAMPLE 90

2000 parts by volume of phosphorus of oxychloride is stirred at 80° to 90°C. A mixture of 277 parts of 5-phenylmercapto-1,8-naphtholactam and 181 parts of aminoterephthalic acid is added thereto in the course of an hour. The whole is boiled under reflux for four hours, allowed to cool and the reaction mixture is then stirred into 5000 parts of ice; the dye deposited is suction filtered and washed with hot water and dried. 418 parts of a compound of formula (XI):

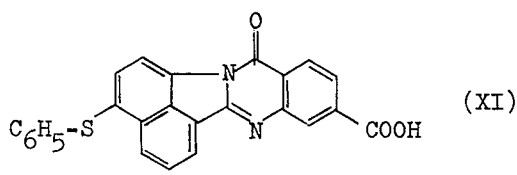

is obtained which dyes polyester greenish yellow hues having good fastness properties.

Table 4 gives dyes of the constitution (VII)

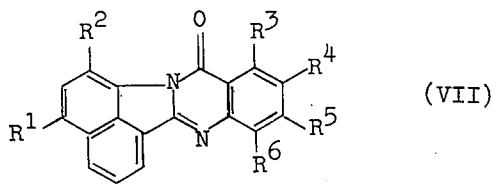

which can be prepared by the methods of Examples 89 and 90.

1,6-hexanediol. 20 parts of p-toluenesulfonic acid is added and the whole is stirred for twelve hours at 130°C. The whole is diluted with 500 parts of methanol during cooling and then suction filtered and the product dried. 39 parts of a dye of the constitution (VII) with $R^1$ equal to $SC_6H_5$, $R^5$ equal to $COO(CH_2)_6OH$ and $R^2$, $R^3$, $R^4$, $R^6$, $R^7$ and $R^8$ equal to H is obtained which gives greenish yellow dyeings having good fastness properties on polyester.

EXAMPLE 110

42.2 parts of the carboxylic acid of Example 90, 20 parts of thionyl chloride and 1 part of dimethylformamide are introduced into 300 parts of anhydrous chlorobenzene. The whole is boiled under reflux for six hours and then about 100 parts of solvent is distilled off in vacuo. 19 parts of morpholine is added and the whole is boiled for another two hours. The remainder of the chlorobenzene is then distilled off with steam. The dye suspension is suction filtered and the dye is washed with water and dried. 46 parts of a compound of the formula (VII) with $R^1$ equal to $-SC_6H_5$, $R^5$ equal to

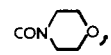

and $R^2$, $R^3$, $R^4$, $R^6$, $R^7$ and $R^8$ equal to H are obtained which dye polyester yellow hues having good fastness properties.

EXAMPLE 111

A mixture of 250 parts by volume of dimethylformamide, 45.7 parts of the dye of Example 92, 14 parts of 4-methylthiophenol and 16 parts of anhydrous potassium carbonate is boiled under reflux for ten hours. 150 parts of water and 5 parts of acetic acid are added to the reaction mixture during cooling. The dye thus crystallized out. It is suction filtered, washed with water and dried. 46.2 parts of a compound of the formula (VII) with $R^1$ equal to $—SC_6H_4CH_3$ (4') and $R^2$, $R^3$, $R^5$ and $R^6$ equal to H is obtained which gives reddish yellow dyeings having a high level of fastness on polyester.

EXAMPLE 112

41.3 parts of the dye of Example 107, 15 parts of

TABLE 4

| Example | $R^1$ | $R^2$ | $R^3$ | $R^4$ | $R^5$ | $R^6$ | Hue on polyester |
|---|---|---|---|---|---|---|---|
| 91 | $-SC_6H_5$ | H | H | Cl | H | H | greenish yellow |
| 92 | $-SC_6H_5$ | H | H | Br | H | H | yellow |
| 93 | $-SC_6H_5$ | H | Cl | H | H | Cl | yellow |
| 94 | $-SC_6H_4CH_3$ (4') | H | H | Cl | H | Cl | yellow |
| 95 | $-SC_6H_5$ | H | H | Br | H | Br | yellow |
| 96 | $-SC_6H_5$ | H | H | $NO_2$ | H | H | yellow |
| 97 | $-SC_6H_4OCH_3$ (4') | H | H | $NO_2$ | H | H | reddish yellow |
| 98 | $-SC_6H_5$ | H | H | $NO_2$ | H | Cl | yellow |
| 99 | $-SC_6H_5$ | H | H | $NO_2$ | H | Br | yellow |
| 100 | $-SC_6H_4CH_3$ (4') | H | H | Cl | H | $NO_2$ | reddish yellow |
| 101 | $-SC_6H_4Cl$ (4') | H | H | Br | H | $NO_2$ | yellow |
| 102 | $-SC_6H_5$ | H | Cl | H | H | $NO_2$ | yellow |
| 103 | $-SC_6H_5$ | $-SC_6H_5$ | H | Cl | H | H | yellow |
| 104 | $-SC_6H_4CH_3$ (4') | $-SC_6H_4CH_3$ (4') | H | $NO_2$ | H | H | reddish yellow |
| 105 | $-SC_6H_5$ | H | H | $-CH_3$ | H | H | yellow |
| 106 | $-SC_6H_4Cl$ (4') | H | H | $-OC_2H_5$ | H | H | yellow |
| 107 | Cl | $-SC_6H_5$ | H | H | H | H | greenish yellow |
| 108 | Cl | $-SC_6H_5$ | H | $NO_2$ | H | H | yellow |

EXAMPLE 109

42.2 parts of the carboxylic acid obtained according to Example 90 is introduced into 200 parts of molten 4-chlorothiophenol and 16 parts of anhydrous potassium carbonate are introduced into 250 parts by volume of N-methylpyrrolidone. After boiling for six hours under reflux the whole is worked up as described in Example 111. 46.8 parts of a dye of the formula (VII) with $R^1$ equal to —$SC_6H_4Cl$ (4'), $R^2$ equal to —$SC_6H_5$ and $R^3$ to $R^6$ equal to H is obtained with which yellow dyeings are obtained on polyester.

EXAMPLE 113

39.3 parts of the compound obtained according to Example 77 is boiled in 200 parts by volume of glacial acetic acid. 50 parts of water and 30 parts of concentrated hydrochloric acid are added and the whole is then cooled to 0°C and a solution of 7 parts of sodium nitrite in 37.5 parts of water is dripped in. The whole is stirred for another four hours and the temperature is kept at from 0° to 5°C by adding 100 parts of ice. The diazonium salt solution is filtered and dripped within fifteen minutes into a boiling mixture of 100 parts of crystallized cupric sulfate and 1000 parts of 10% acetic acid. The reaction product is thus precipitated in the form of a dark red deposit. The whole is boiled for another hour and the precipitate is suction filtered while hot, washed until neutral with hot water and dried. 36.2 parts of a compound of the constitution (XII) with $R^3$, $R^4$, $R^5$, $R^6$, $R^{10}$ and $R^{11}$ all equal to H:

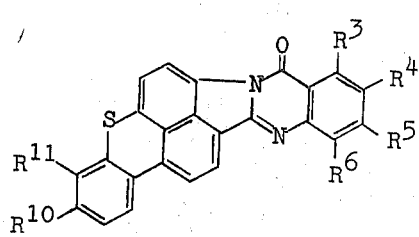

(XII)

is obtained; it has a melting point of 338°C after it has been recrystallized from N-methylpyrrolidone. The red solutions of the compound exhibit marked fluorescence in the orange range. The dye dyes polyester bright orange red shades having good fastness properties from an aqueous liquor.

The compound (IXa) from Example 77 may also be converted into the cyclized dye analogously. It dyes polyester bright yellowish red hues.

The following thioxanthene derivatives (XII) specified in Table 5 may also be prepared by the method of Example 113:

EXAMPLE 129

A mixture of 138 parts of a compound of the formula (XIII):

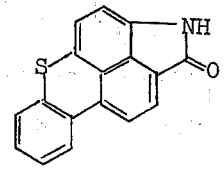

(XIII)

(prepared according to German Patent No. 2,223,937, Example 68 as described below) and 69 parts of anthranilic acid is added in portions to 2000 parts by volume of phosphorus oxychloride at 90°C. The whole is boiled for four hours under reflux, 2000 parts by volume of toluene is added and the whole is allowed to cool. The product is suction filtered, washed with methanol and dried. 176 parts of a dye of the formula (XII) with $R^3$, $R^4$, $R^5$, $R^6$, $R^{10}$ and $R^{11}$ all equal to H is obtained which is identical with the compound specified in Example 113.

Compound XIII is prepared as follows. 146 parts of 5-(2'-aminophenylmercapto)-1,8-naphtolactam is dissolved in 1000 parts of boiling acetic acid, 250 parts of water and 150 parts of concentrated hydrochloric acid are added. The whole is then cooled to 0°C. and diazotized by dripping in a solution of 35 parts of sodium nitrite in 170 parts of water. The whole is stirred for 4 hours at 0°C. to 5°C. and the diazonium salt solution is then allowed to flow into a boiling solution of 500 parts of crystallized cupric sulfate in 5000 parts of 10% acetic acid. The whole is then boiled for 1 hour under reflux and the deposited product is suction filtered while hot and washed with hot water. After drying 136 parts of a red compound of the formula XIII is obtained; after recrystallization from nitrobenzene it has a melting point of 351° – 352°C.

A dye which dyes polystyrene lightfast violet hues is obtained when 3,5-dinitroanthranilic acid is used instead of anthranilic acid.

If the anthranitic acid in Example 129 is replaced by an equivalent amount of a substituted anthranilamide the dyes of formula (XIVA) set out in Table 6 are obtained. Because of their high melting points and low solubility these compounds have only low affinity for polyester fibers but are outstandingly suitable for color-

| Example | $R^3$ | $R^4$ | $R^5$ | $R^6$ | $R^{10}$ | $R^{11}$ | Hue on polyester |
|---------|-------|-------|-------|-------|----------|----------|------------------|
| 114 | H | H | H | H | —$CH_3$ | H | yellowish red |
| 115 | H | H | H | H | H | —$CH_3$ | yellowish red |
| 116 | H | H | H | H | —$OCH_3$ | H | red |
| 117 | H | H | H | H | —$C_2H_5$ | H | red |
| 118 | —$CH_3$ | H | H | H | H | H | orange |
| 119 | H | —$CH_3$ | H | H | H | H | orange |
| 120 | H | —$OCH_3$ | H | H | H | H | red |
| 121 | H | H | —$OC_2H_5$ | H | H | H | yellowish red |
| 122 | H | H | H | —$OCH_3$ | H | H | yellowish red |
| 123 | H | H | —$COOC_5H_{11}$ | H | H | H | orange |
| 124 | H | H | —$COO(CH_2)_2OH$ | H | H | H | orange |
| 125 | H | H | —$CON(C_4H_9)_2$ | H | H | H | orange |
| 126 | H | H | —CON⟨⟩ | H | H | H | orange |
| 127 | H | H | —$COC_6H_5$ | H | H | H | orange |
| 128 | H | H | —$COC_6H_4C_4H_9$ (p) | H | H | H | orange | ing plastics, as for example polystyrene, in the hues given in the Table:

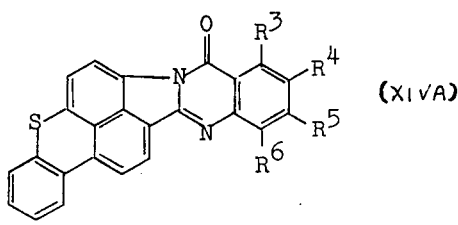

(XIVA)

TABLE 6

| Ex. | $R^3$ | $R^4$ | $R^5$ | $R^6$ | Hue in polystyrene |
|---|---|---|---|---|---|
| 130 | —CH₃ | H | H | H | yellow |
| 131 | H | —CH₃ | H | H | orange |
| 132 | H | —OCH₃ | H | H | orange |
| 133 | H | H | —OC₂H₅ | H | yellowish red |
| 134 | H | H | H | —OCH₃ | orange |
| 135 | Cl | H | H | Cl | orange |
| 136 | H | Cl | H | H | reddish orange |
| 137 | H | Cl | H | Cl | reddish orange |
| 138 | H | Br | H | H | red |
| 139 | H | Br | H | Br | red |
| 140 | H | NO₂ | H | H | red |
| 141 | H | NO₂ | H | Cl | red |
| 142 | H | NO₂ | H | Br | red |
| 143 | H | Cl | H | NO₂ | Bordeaux |
| 144 | H | Br | H | NO₂ | Bordeaux |
| 145 | Cl | H | H | NO₂ | reddish violet |
| 146 | H | H | —COOH | H | red |

EXAMPLE 147

45.5 parts of the dye prepared according to Example 138, 13 parts of thiophenol and 16 parts of potassium carbonate are introduced into 600 parts by volume of N-methylpyrrolidone and boiled under reflux for six hours. The whole is diluted during cooling with 200 parts by volume of ethanol and 100 parts by volume of 20% acetic acid. The product is then suction filtered, washed with hot water and dried. 38.3 parts of a dye of the formula (XIVA) in which $R^3$, $R^5$ and $R^6$ are equal to H and $R^4$ is equal to SC₆H₅ is obtained. It colors polystyrene bright red hues.

EXAMPLE 148

42.0 parts of the carboxylic acid of Example 146 is introduced into 400 parts by volume of anhydrous nitrobenzene. 50 parts of thionyl chloride and 2 parts of dimethylformamide are added and the whole is stirred for twenty-four hours at 125°C. The product is then suction filtered, washed with benzene and dried. 41.8 parts of the acyl chloride of the formula (XIVA) is obtained with $R^3$, $R^4$ and $R^6$ equal to H and $R^5$ equal to COCl and with a chlorine content of 7.8% (calculated 8.1%).

EXAMPLE 149

A mixture of 200 parts by volume of dehydrated dichlorobenzene, 10 parts of pentanediol-(1,5), 4 parts of pyridine and 22 parts of the acyl chloride of Example 148 is boiled under reflux for four hours. After cooling the whole is diluted with 100 parts by volume of methanol, suction filtered and the product is washed with methanol and dried. 24 parts of dye of the formula (XIVA) with $R^3$, $R^4$ and $R^6$ equal to H and $R^5$ equal to COO(CH₂)₅OH is obtained which is identical with the dye of Example 124.

EXAMPLE 150

10 parts of 3-ethoxypropylamine, 6 parts of triethylamine and 22 parts of the carboxylic acid chloride of Example 148 are introduced into 150 parts by volume of dimethylformamide. The mixture is stirred for two hours at 150°C, then diluted with 100 parts of ethanol and suction filtered. After having been washed with ethanol and dried 21 parts of dye of the formula (XIVA) in which $R^3$, $R^4$ and $R^6$ are equal to H and $R^5$ is equal to CONHCH₂CH₂CH₂OC₂H₅ is obtained which goes onto polyester in orange hues.

Other esters and amides of the formula (XIVB) which are prepared from the acyl chloride of Example 148 are set out in Table 7:

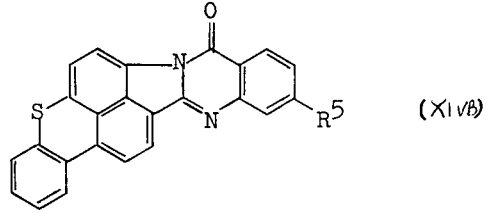

(XIVB)

They all give orange hues on polyesters.

TABLE 7

| Example | $R^5$ |
|---|---|
| 151 | —COOCH₂CH₂OC₄H₉ |
| 152 | —COOCH₂CH₂OCH₂CH₂OH |
| 153 | —COO(CH₂)₃OH |
| 154 | —COO(CH₂)₆OH |
| 155 | —CONHC₄H₉ |
| 156 | —CONHCH₂CH₂CH₂OH |
| 157 | —CONH(CH₂)₆OH |
| 158 | —CONH(CH₂)₂CN |
| 159 | —CONHCH₂CH(CH₂)₃CH₃<br>             C₂H₅ |
| 160 | —CON⟨CH₃ / CH₂CH₂OH |
| 161 | —CON(CH₂CH₂OH)₂ |
| 162 | —CON⟨C₆H₁₁⟩ |

EXAMPLE 163

37.8 parts of the dye of Example 9 is boiled in 300 parts of anhydrous chlorobenzene so that the dye dissolves. 20 parts of dimethyl sulfate is then allowed to flow in and boiling is continued for another four hours under reflux and then allowed to cool. The product is suction filtered, washed with acetone and dried. 42 parts of the dye of formula (XV) in which $R^4$ is equal to SC₆H₅, $R^1$, $R^2$, $R^3$, $R^5$ and $R^6$ are equal to H, R is equal to CH₃ and X⁻ is CH₃SO₄ is obtained in the form of yellow-red crystals which dye polyacrylonitrile from an aqueous liquor bright reddish yellow hues having good fastness properties.

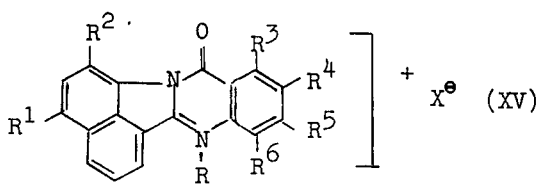

(XV)

Other quaternary dyes of the formula (XV) and their hues on polyacrylonitrile are given in the following Table 8:

TABLE 8

| Example | R | | Hue on polyacrylonitrile |
|---|---|---|---|
| 164 | —C$_2$H$_5$ | R$^4$ = —SC$_6$H$_4$CH$_3$ (4'); R$^1$ = R$^2$ = R$^3$ = R$^5$ = R$^6$ = H | yellowish orange |
| 165 | —CH$_3$ | R$^1$ = —SC$_6$H$_4$Cl (4'); R$^2$ = R$^2$ = R$^3$ = R$^5$ = R$^6$ = H | yellow |
| 166 | —CH$_2$CH$_2$OH | R$^1$ = SC$_6$H$_5$; R$^2$ = R$^3$ = R$^4$ = R$^5$ = R$^6$ = H | orange |
| 167 | —CH$_3$ | R$^1$ = SC$_6$H$_4$OCH$_3$ (4'); R$^2$ = R$^3$ = R$^4$ = R$^5$ = R$^6$ = H | orange |
| 168 | —CH$_2$C$_6$H$_5$ | R$^1$ = SC$_6$H$_4$CH$_3$ (4'); R$^2$ = R$^3$ = R$^4$ = R$^5$ = R$^6$ = H | orange |
| 169 | —CH$_3$ | R$^1$ = R$^4$ = —SC$_6$H$_5$; R$^2$ = R$^3$ = R$^5$ = R$^6$ = H | orange |
| 170 | —C$_2$H$_5$ | R$^1$ = R$^4$ = —SC$_6$H$_4$OCH$_3$; R$^2$ = R$^3$ = R$^5$ = R$^6$ = H | reddish orange |
| 171 | —CH$_3$ | R$^1$ = R$^2$ = —SC$_6$H$_5$; R$^3$ = R$^4$ = R$^5$ = R$^6$ = H | reddish orange |
| 172 | —CH$_2$CHOHCH$_3$ | R$^1$ = R$^2$ = —SC$_6$H$_4$CH$_3$; R$^3$ = R$^4$ = R$^5$ = R$^6$ = H | reddish orange |
| 173 | —CH$_3$ | R$^3$ = R$^6$ = —SC$_6$H$_5$; R$^1$ = R$^2$ = R$^4$ = R$^5$ = H | yellow |
| 174 | —C$_2$H$_5$ | R$^4$ = R$^6$ = —SC$_6$H$_5$; R$^1$ = R$^2$ = R$^3$ = R$^5$ = H | yellow |

EXAMPLE 175

37.6 parts of the dye of Example 113 is suspended in 500 parts by volume of anhydrous nitrobenzene and stirred at 125°C. 16 parts of dimethyl sulfate is added and stirring is continued for another six hours at 125°C. After cooling, the whole is suction filtered and the product is washed with methanol and dried. 34.6 parts of the dye of the formula (XVI)

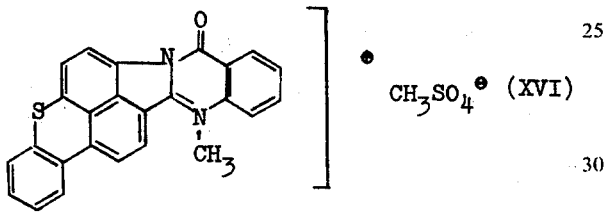

is obtained with which reddish violet dyeings are obtained on polyacrylonitrile.

EXAMPLE 176

A mixture of 120 parts by volume of anhydrous nitrobenzene, 277 parts of 5-phenylmercapto-1,8-naphtholactam and 227 parts of 2-amino-3,5-dinitrobenzoic acid is stirred at 100°C. 200 parts of phosphorus oxychloride is dripped in within an hour. The whole is stirred for six hours at 110°C, 250 parts of saturated sodium acetate solution is added and the nitrobenzene is distilled off with steam. The dye is suction filtered, washed with water and dried. 439 parts of the compound of the formula

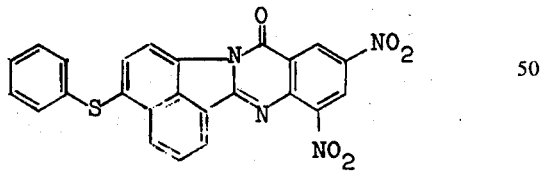

is obtained which dyes polyesters orange hues having excellent fastness properties.

I claim:

1. A compound of the formula

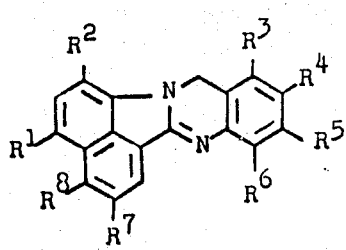

in which:

R$^1$ is hydrogen; chloro; methyl; methoxy; ethoxy; phenoxy; benzoyl; benzoyl mono-substituted by chloro, bromo, methyl, methoxy or cyano; sulfamoyl; sulfamoyl substituted at the nitrogen once or twice by methyl, ethyl, propyl, butyl, β-hydroxyethyl, γ-methoxypropyl or β-ethylhexyl; sulfopyrrolidide; sulfopiperidide; sulfomorpholide; sulfopiperazide; naphthylmercapto; phenylmercapto; phenylmercapto di-substituted by chloro; phenylmercapto mono-substituted by methyl, methoxy, ethoxy, acetylamino, trifluoromethyl, carbalkoxy with 1 to 4 carbon atoms in the alkoxy, carbo-β-hydroxyethoxy or carbo-β-methoxyethoxy; o-aminophenylmercapto; or o-aminophenylmercapto mono-substituted by methyl, ethyl or methoxy;

R$^2$ is hydrogen, chloro; naphthylmercapto; phenylmercapto; phenylmercapto di-substituted by chloro; phenylmercapto mono-substituted by methyl, methoxy, ethoxy, acetylamino, trifluoromethyl, carbalkoxy with 1 to 4 carbon atoms in the alkoxy, carbo-β-hydroxyethoxy or carbo-β-methoxyethoxy; o-aminophenylmercapto; or o-aminophenylmercapto mono-substituted by methyl, ethyl or methoxy;

R$^3$ is hydrogen; chloro; methyl; carboxyl; carbamoyl; carbamoyl substituted at the nitrogen once or twice by alkyl of 1 to 4 carbon atoms, β-hydroxyethyl, γ-methoxypropyl or β-ethylhexyl; carbopyrrolidide; carbopiperidide; carbomorpholide; carbopiperazide; carbalkoxy with 1 to 8 carbon atoms in the alkoxy; carbo-β-hydroxyethoxy; carbo-ω-hydroxyhexoxy; carbo-β-methoxyethoxy; carbo-β-butoxyethoxy; carbo-β-(β'-methoxyethoxy)ethoxy; benzoyl; benzoyl mono-substituted by chloro, bromo, methyl or methoxy; naphthylmercapto; phenylmercapto; phenylmercapto di-substituted by chloro; phenylmercapto mono-substituted by methyl, methoxy, ethoxy, acetylamino, trifluoromethyl, carbalkoxy with 1 to 4 carbon atoms in the alkoxy, carbo-β-hydroxyethoxy or carbo-β-methoxyethoxy; o-aminophenylmercapto; or o-aminophenylmercapto mono-substituted by methyl, ethyl or methoxy;

R$^4$ is hydrogen; chloro; bromo; nitro; methyl; methoxy; ethoxy; the carboxylic esters or amides specified for R$^3$; naphthylmercapto; phenylmercapto; phenylmercapto di-substituted by chloro; phenylmercapto mono-substituted by methyl, methoxy, ethoxy, acetylamino, trifluoromethyl, carbalkoxy with 1 to 4 carbon atoms in the alkoxy, carbo-β-hydroxyethoxy or carbo-β-methoxyethoxy; o-aminophenylmercapto; or o-aminophenylmercapto mono-substituted by methyl, ethyl or methoxy;

R$^5$ is hydrogen; methoxy; ethoxy; the carboxylic esters or amides specified for $R^3$; naphthylmercapto; phenylmercapto; phenylmercapto di-substituted by chloro; phenylmercapto mono-substituted by methyl, methoxy, ethoxy, acetylamino, trifluoromethyl, carbalkoxy with 1 to 4 carbon atoms in the alkoxy, carbo-$\beta$-hydroxyethoxy or carbo-$\beta$-methoxyethoxy; o-aminophenylmercapto; or o-aminophenylmercapto mono-substituted by methyl, ethyl or methoxy;

$R^6$ is hydrogen; chloro; bromo; nitro; methyl; methoxy; naphthylmercapto; phenylmercapto; phenylmercapto di-substituted by chloro; phenylmercapto mono-substituted by methyl, methoxy, ethoxy, acetylamino, trifluoromethyl, carbalkoxy with 1 to 4 carbon atoms in the alkoxy, carbo-$\beta$-hydroxyethoxy or carbo-$\beta$-methoxyethoxy; o-aminophenylmercapto; or o-aminophenylmercapto mono-substituted by methyl, ethyl or methoxy;

$R^7$ and $R^8$ are hydrogen; methoxy; or ethoxy;

$R^1$ and $R^8$ together are

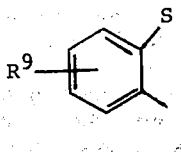

and $R^9$ is hydrogen; methyl; methoxy; or ethoxy;

with the proviso that only one or two of $R^1$ to $R^6$ may represent said naphthyl and phenylmercapto members.

2. A compound as claimed in claim 1 wherein one of $R^3$ to $R^6$ is nitro; benzoyl; benzoyl monosubstituted by chloro, bromo, methyl or methoxy; or a carboxylic ester or amide as specified for $R^3$.

3. A compound as claimed in claim 1 wherein $R^1$ is benzoyl; benzoyl mono-substituted by chloro, bromo, methyl, methoxy or cyano; sulfamoyl; sulfamoyl substituted at the nitrogen once or twice by methyl, ethyl, propyl, butyl, $\beta$-hydroxyethyl, $\gamma$-methoxypropyl or $\beta$-ethylhexyl; and wherein at least one of $R^4$ and $R^6$ is naphthylmercapto; phenylmercapto; phenylmercapto di-substituted by chloro; phenylmercapto mono-substituted by methyl, methoxy, ethoxy, acetylamino, trifluoromethyl, carbalkoxy with 1 to 4 carbon atoms in the alkxoy, carbo-$\beta$-hydroxyethoxy or carbo-$\beta$-methoxyethoxy; o-aminophenylmercapto; or o-aminophenylmercapto mono-substituted by methyl, ethyl or methoxy.

* * * * *